(12) United States Patent
Schuch et al.

(10) Patent No.: US 9,416,079 B2
(45) Date of Patent: *Aug. 16, 2016

(54) PROCESS FOR PREPARING 4-CYCLOHEXYL-2-METHYL-2-BUTANOL

(71) Applicant: BASF SE, Ludwigshafen (DE)

(72) Inventors: Rudolf Schuch, Schriesheim (DE); Stefan Rüdenauer, Worms (DE); Klaus Ebel, Lampertheim (DE); Ralf Pelzer, Fürstenberg (DE); Andreas Keller, Speyer (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,948

(22) Filed: May 12, 2015

(65) Prior Publication Data

US 2015/0246864 A1 Sep. 3, 2015

Related U.S. Application Data

(62) Division of application No. 13/616,147, filed on Sep. 14, 2012, now Pat. No. 9,056,812.

(60) Provisional application No. 61/535,381, filed on Sep. 16, 2011.

(51) Int. Cl.
| | |
|---|---|
| *C07C 33/18* | (2006.01) |
| *C07C 29/44* | (2006.01) |
| *C07C 29/19* | (2006.01) |
| *C07C 29/80* | (2006.01) |
| *B01J 23/46* | (2006.01) |
| *B01J 23/56* | (2006.01) |
| *B01J 35/10* | (2006.01) |
| *B01J 37/18* | (2006.01) |
| *B01J 21/08* | (2006.01) |
| *B01J 33/00* | (2006.01) |
| *B01J 35/00* | (2006.01) |
| *B01J 35/02* | (2006.01) |
| *B01J 35/08* | (2006.01) |
| *B01J 37/02* | (2006.01) |

(52) U.S. Cl.
CPC ............... *C07C 29/44* (2013.01); *B01J 23/462* (2013.01); *B01J 23/56* (2013.01); *B01J 35/1019* (2013.01); *B01J 35/1042* (2013.01); *B01J 35/1061* (2013.01); *C07C 29/19* (2013.01); *C07C 29/80* (2013.01); *B01J 21/08* (2013.01); *B01J 33/00* (2013.01); *B01J 35/008* (2013.01); *B01J 35/0026* (2013.01); *B01J 35/023* (2013.01); *B01J 35/08* (2013.01); *B01J 35/108* (2013.01); *B01J 37/0203* (2013.01); *B01J 37/18* (2013.01); *C07C 2101/14* (2013.01)

(58) Field of Classification Search
USPC ........................................ 568/822, 823, 825
See application file for complete search history.

(56) References Cited

U.S. PATENT DOCUMENTS

| | | | |
|---|---|---|---|
| 3,027,398 A | 3/1962 | Foohey | |
| 4,056,541 A | 11/1977 | Hoffman et al. | |
| 4,701,278 A | 10/1987 | Fehr | |
| 4,847,394 A | 7/1989 | Schuster | |
| 5,936,126 A | 8/1999 | Ruhl et al. | |
| 6,284,917 B1 | 9/2001 | Brunner et al. | |
| 6,924,385 B2 | 8/2005 | Lettmann et al. | |
| 7,208,545 B1 | 4/2007 | Brunner et al. | |
| 7,355,084 B2 | 4/2008 | Bottcher et al. | |
| 7,361,714 B2 | 4/2008 | Grass et al. | |
| 8,450,534 B2 * | 5/2013 | Ebel ......................... | C07C 33/20 568/715 |
| 2002/0019559 A1 | 2/2002 | Brunner et al. | |
| 2003/0149310 A1 | 8/2003 | Gerlach et al. | |
| 2004/0097752 A1 | 5/2004 | Lettmann et al. | |
| 2004/0199033 A1 | 10/2004 | Bottcher et al. | |
| 2006/0183936 A1 | 8/2006 | Grass et al. | |
| 2007/0112210 A1 | 5/2007 | Arndt et al. | |
| 2007/0149793 A1 | 6/2007 | Arndt et al. | |
| 2010/0152436 A1 | 6/2010 | Laar et al. | |
| 2011/0237684 A1 * | 9/2011 | Ebel et al. ............... | C07C 33/20 514/772 |
| 2014/0163117 A1 | 6/2014 | Rudenauer et al. | |

FOREIGN PATENT DOCUMENTS

| | | |
|---|---|---|
| DE | 4407019 A1 | 9/1994 |
| DE | 4407091 C1 | 8/1995 |
| EP | 258789 A2 | 3/1988 |
| EP | 0813906 A2 | 12/1997 |
| EP | 1042273 A1 | 10/2000 |

(Continued)

OTHER PUBLICATIONS

A. F. Thomas et al., "Homologues of p=Menthane Derivatives in Roman Camomile", Helvetica Chimica Acta, Bd. 64, Nr. 5, Jul. 22, 1981.
E. L. Bonifaz et al., "Antiproliferative activity of synthetic naphthoquinones related to lapachol. First synthesis of 5-hydroxylapachol", Bioorganic & Medicinal Chemistry, Pergamon, GB, Bd. 18, Nr. 7, Apr. 1, 2010.
English Translation of Chinese Office Action issued on Feb. 2, 2015 for Chinese Application No. 201280044232.6.
International Search Report and Written Opinion issued in PCT/EP2012/062183, dated Sep. 19, 2012, no English translation.

(Continued)

*Primary Examiner* — Pancham Bakshi
(74) *Attorney, Agent, or Firm* — Drinker Biddle & Reath LLP

(57) ABSTRACT

A process for preparing 4-cyclohexyl-2-methyl-2-butanol, comprising:
a) reaction of styrene with isopropanol at elevated temperature to obtain 2-methyl-4-phenyl-2-butanol, and
b) heterogeneously catalyzed hydrogenation of 2-methyl-4-phenyl-2-butanol over a catalyst suitable for ring hydrogenation of aromatics,
where the molar ratio of the styrene used in step a) to the isopropanol used in step a) is in the range from 1:below 5 to 1:0.5.

7 Claims, No Drawings

(56) References Cited

FOREIGN PATENT DOCUMENTS

| EP | 1317959 | A1 | 6/2003 |
|---|---|---|---|
| EP | 1420012 | A1 | 5/2004 |
| JP | 2010095447 | A | 4/2010 |
| WO | WO-99/32427 | A1 | 7/1999 |
| WO | WO-00/78704 | A1 | 12/2000 |
| WO | WO-02/100536 | A1 | 12/2002 |
| WO | WO-03/103830 | A1 | 12/2003 |
| WO | WO-2005/061105 | A1 | 7/2005 |
| WO | WO-2005/061106 | A1 | 7/2005 |
| WO | WO-2006/136541 | A2 | 12/2006 |
| WO | WO-2008066299 | A1 | 6/2008 |
| WO | WO-2008133441 | A1 | 11/2008 |
| WO | PCT/EP2011/054559 | | 3/2011 |
| WO | WO-2011117360 | A2 | 9/2011 |

OTHER PUBLICATIONS

International Search Report dated Dec. 18, 2012 for International Application No. PCT/EP2012/067655.

International Search Report dated Jun. 16, 2011, in International Application No. PCT/EP2011/054559.

International Search Report issued in PCT/EP2012/062183, dated Sep. 19, 2012, no English translation.

Kamitanaka, T., et al., "Direct addition of supercritical alcohols, acetone or acetonitrile to the alkenes without catalysts," Tetrahedron Letters, (2007), vol. 48, pp. 8460-8463.

L. L. Zakharkin et al., "Syntheses of 2-oxabicyclo [4.10.0] hexadec-1 (6)-enefrom cyclododeeanone", Russian Chemical Bulletin, Bd. 43, Nr. 4, Apr. 4, 1994.

Libo Ruan et al., "Synthesis of New Fragrance-Coranol and Its Acetate", Fine Chemicals, vol. 26, No. 12, pp. 1211-1214 (Dec. 15, 2009).

M. Danet et al., "Enantioselective Synthesis of the Originally Proposed Usneoidone Structure: Evidence for a Structural Revision", European Journal of Organic Chemistry, Bd. 2004, Nr. 9, May 1, 2004.

Nakagawa et al "Reactions of supercritical alcohols with unsaturated hydrocarbons", Journal of Supercritical Fluids, Bd. 27, Nr. 3, pp. 255-261 (2003).

Siewert, G., et al., "Hydroxylierung von 5-Alkyl-2-(benzolsulfonylamino)pyrimidinen und strukturverwandten Antidiabetika," Chem. Ber., (1973), vol. 106, pp. 1290-1302.

Okazawa, et al., "Solution carbocation stabilities measured by internal competition for a hydride ion", Can. J. Chem., vol. 60, pp. 2180-2193, 1982.

* cited by examiner

PROCESS FOR PREPARING 4-CYCLOHEXYL-2-METHYL-2-BUTANOL

CROSS-REFERENCE TO RELATED APPLICATIONS

This application is a divisional application of U.S. patent application Ser. No. 13/616,147, filed Sep. 14, 2012. U.S. patent application Ser. No. 13/616,147 claims benefit under 35 U.S.C. §119(e) of U.S. Provisional Patent App. Ser. No. 61/535,381, filed Sep. 16, 2011, which is incorporated herein by reference in its entirety.

The present invention relates to a process for preparing 4-cyclohexyl-2-methyl-2-butanol.

4-Cyclohexyl-2-methyl-2-butanol, which is also known as coranol, is a fragrance with a lily-of-the-valley odor, the use of which as a constituent of fragrance compositions was described for the first time in U.S. Pat. No. 4,701,278.

The preparation of 4-cyclohexyl-2-methyl-2-butanol was described by N. E. Okazawa et al. in Can. J. Chem. 60 (1982), 2180-93 and comprises the conversion of 3-cyclohexylpropanoic acid to the acid chloride, which is then reacted with 2 mol of methyllithium to give 4-cyclohexyl-2-methyl-2-butanol. Owing to the use of methyllithium, this preparation process, especially in the case of performance on a larger scale, is afflicted with not inconsiderable risks and is economically unattractive. Nevertheless, no further preparation processes have been described to date in the literature.

Unpublished application PCT/EP2011/054559 to the applicant describes a process for preparing 4-cyclohexyl-2-methyl-2-butanol. The process described therein discloses the reaction of styrene with isopropanol at elevated temperature. Examples 1 to 4 disclose a reaction of styrene with isopropanol, wherein the isopropanol is added batchwise to the reaction. The conversion in examples 1 to 4 is always more than 85%, and so the molar ratios of styrene to isopropanol in examples 1 to 4 are always well above 1:5.

It is therefore an object of the present invention to provide an economically viable process for preparing 4-cyclohexyl-2-methyl-2-butanol. This object is achieved by the process described hereinafter, which comprises the following steps:

a) reaction of styrene with isopropanol at elevated temperature to obtain 2-methyl-4-phenyl-2-butanol, and b) heterogeneously catalyzed hydrogenation of 2-methyl-4-phenyl-2-butanol over a catalyst suitable for ring hydrogenation of aromatics, where the molar ratio of the styrene used in step a) to the isopropanol used in step a) is in the range from 1:below 5 to 1:0.5.

The process can be represented by the following reaction scheme:

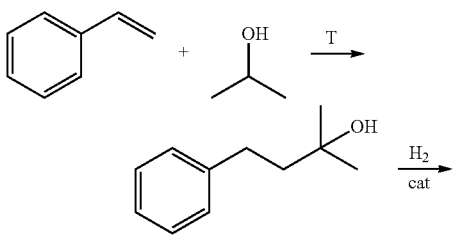

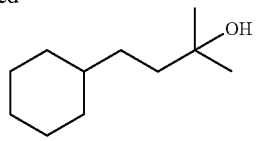

The invention thus relates to a process for preparing 4-cyclohexyl-2-methyl-2-butanol with the steps described here and hereinafter and in the claims.

The process is associated with a series of advantages. It allows the preparation of 4-cyclohexyl-2-methyl-2-butanol from very inexpensive commodity chemicals. The use of expensive and hazardous reagents such as methyllithium is not required. Both step a) and step b) can be performed without any problem on the industrial scale, and afford the particular products with high selectivity and good yields.

In step a) of the process according to the invention, isopropanol is reacted with styrene at elevated temperature. This forms 2-methyl-4-phenyl-2-butanol in the manner of a hydroxyalkylation, and by-products including toluene and ethylbenzene, which can, however, be removed from the target product, for example, by distillation.

In the context of an analytical study of the reaction of styrene with alkanols under supercritical conditions, the reaction was reported by T. Nakagawa et al. (see J. Supercritical Fluids, 27 (2003), p. 255-261 and Tetrahedron Lett., 48 (2007), p. 8460-8463). However, the reaction was not utilized to preparatively obtain 2-methyl-4-phenyl-2-butanol.

With regard to the selectivity of the reaction, it has been found to be advantageous when reaction in step a) is performed under supercritical conditions. This is understood to mean reaction conditions under which at least one of the components of the reaction mixture, preferably the isopropanol, is in the supercritical state. Accordingly, in a preferred embodiment of the process according to the invention, the reaction in step a) is effected under conditions under which isopropanol is in the supercritical state. The critical temperature $T_c$ of isopropanol is 235° C.; the critical pressure $P_c$ is 4.8 MPa. Supercritical conditions can be established by the person skilled in the art by varying pressure and temperature.

The temperature required for a sufficient rate of the reaction of styrene with isopropanol is generally at least 250° C., frequently at least 300° C. and especially at least 320° C. To achieve a sufficient selectivity of the reaction, it has been found to be advantageous when the temperature of the reaction does not exceed a value of 500° C. The reaction in step a) is effected preferably at elevated pressure, which is generally in the range from 5 to 50 MPa, frequently in the range from 10 to 30 MPa and especially in the range from 15 to 25 MPa. The pressure in the reaction vessel can be adjusted by charging with an inert substance. The reaction is preferably effected under the autogenous pressure of the reaction mixture which exists at the desired reaction temperature.

By its nature, the reaction time depends on the conditions selected and the conversion desired, and is typically in the range from 30 sec to 4 h, particularly in the range from 3 min to 3 h and especially in the range from 5 min to 2.5 h. In general, the reaction is conducted to such an extent that the reactant used in deficiency, which is preferably styrene, is converted to an extent of at least 80%, especially to an extent of at least 90%.

In one embodiment of the invention, the reaction time is in the range from 30 min to 4 h, particularly in the range from 1 to 3 h and especially in the range from 1.5 to 2.5 h. In general, the reaction is conducted to such an extent that the reactant used in deficiency, which is preferably styrene, is converted to an extent of at least 80%, especially to an extent of at least 90%.

It has been found to be particularly advantageous to perform the reaction of step a) at elevated temperatures, i.e. above 300° C., especially above 320° C., especially in the range of 350° C. and 500° C., preferably in the range of 390° C. and 500° C. This allows short reaction times, which are typically in the range from 30 sec to 30 min, particularly in the range from 3 min to 20 min and especially in the range from 5 min to 15 min. In this way, even at a high styrene conversion, selectivities based on the target product of distinctly >60% can be achieved.

With regard to the selectivity of the reaction, it has been found to be advantageous when the reaction in step a) is performed in substantial or complete absence of catalysts, for example free-radical initiators, acids or transition metal compounds. "Substantial absence" means that the concentration of any catalysts is less than 1 g/kg (<1000 ppm), especially less than 0.1 g/kg (<100 ppm), based on the total weight of the reaction mixture.

The reaction of styrene with isopropanol in step a) can be performed in bulk or in a suitable diluent, i.e. one which is inert under reaction conditions. Suitable inert diluents are aprotic organic solvents which do not have an ethylenically unsaturated double bond, for example aliphatic and alicyclic ethers having preferably 4, 5 or 6 carbon atoms, aliphatic and cycloaliphatic saturated hydrocarbons having preferably 6 to 8 carbon atoms, alkyl esters of aliphatic carboxylic acids having preferably 4 to 8 carbon atoms, and mixtures of the aforementioned solvents. Preference is given to effecting the reaction in step a) in substance, i.e. essentially no feedstocks other than styrene and isopropanol, for example inert solvents, are used for the reaction. "Essentially" means here that styrene and isopropanol make up at least 95% by weight, especially at least 99% by weight, based on the total amount of the components used in step a). In addition, the reactants used for the reaction, i.e. styrene and isopropanol, as a result of the preparation, may comprise small amounts of impurities such as water, ethylbenzene, toluene and the like, in which case the impurities generally make up less than 5% by weight, especially less than 1% by weight, based on the total amount of the reactants. In particular, the water content of the reactants used in step a) is not more than 1% by weight, based on the total amount of the reactants.

In the process according to the invention, styrene and isopropanol are used in step a) in a molar ratio of styrene to isopropanol 1:below 5 to 1:0.5.

With regard to an efficient reaction regime, it is advantageous when styrene and isopropanol are used in step a) in a molar ratio in the range from 1:4.9 to 1:0.5, especially 1:4.5 to 1:0.5, preferably in the range from 1:4 to 1:0.75 especially in the range from 1:3.5 to 1:1.5, or in the range from 1:2 to 1:1, preferably in the range from 1:1.

The reaction in step a) can be performed in batchwise mode, i.e. styrene and isopropanol are initially charged in a suitable reactor in the desired molar ratio and brought to the desired reaction conditions and held under reaction conditions until the desired conversion. The reaction in step a) can also be performed in what is known as semibatchwise mode, i.e. the majority, generally at least 80%, of one or both reactants is introduced into the reactor under reaction conditions continuously or in portions over a prolonged period, generally at least 50% of the total reaction time. The reaction in step a) can also be performed continuously, i.e. styrene and isopropanol are fed continuously into a reaction zone in the desired molar ratio and the reaction mixture is withdrawn continuously from the reaction zone. The rate at which styrene and isopropanol are supplied to the reaction zone is guided by the desired residence time, which in turn depends in a known manner on the reactor geometry and the above-specified reaction time.

The reaction in step a) can in principle be performed in all reactors suitable for the selected reaction conditions, preferably in autoclaves, which may have apparatus for mixing of the reactants, or in reaction tubes.

In order to keep the molar ratio of styrene to isopropanol low during the reaction and simultaneously to allow an efficient reaction regime, it has been found to be advantageous when at least 80%, especially at least 90%, of the isopropanol used in step a) is initially charged, optionally together with a portion of the styrene, and at least 80%, especially at least 90%, of the styrene used in step a) is fed to the reaction in step a) under reaction conditions. The styrene can be added in portions or preferably continuously. The rate at which styrene is fed in is preferably selected such that the molar ratio of the as yet unreacted styrene fed into the reaction zone or the reactor to the isopropanol present in the reaction zone during the reaction is less than 1:below 5, particularly not more than 1:4.9, especially not more than 1:4.5 and especially not more than 1:4, for example in the range from 1.49 to 1:0.5, especially 1:4.5 to 1:0.5, preferably in the range from 1:4 to 1:0.75 and especially in the range from 1:3.5 to 1:1.5. In a continuous reaction regime, styrene and isopropanol will therefore preferably be supplied to the reactor or to the reaction zone in the aforementioned molar ratios. In an embodiment of the invention, the rate with which styrene is supplied is preferably selected such that the molar ratio of the styrene fed into the reaction zone or the reactor to the isopropanol present in the reaction zone is in the range from 1:below 5, particularly in the range from 1:4.9 to 1:0.5, especially 1:4.5 to 1:0.5, especially more preferably in the range from 1:4 to 1:0.75 and especially in the range from 1:3.5 to 1:1.5, especially 1:2 to 1:1. This is especially true, in the case of a continuous reaction regime too, of the molar ratios of styrene and isopropanol supplied to the reactor or to the reaction zone.

The present invention further provides a process for preparing 2-methyl-4-phenyl-2-butanol, comprising a) the reaction of styrene with isopropanol at elevated temperature, where the molar ratio of the styrene used in step a) to the isopropanol used in step a) is in the range from 1:below 5 to 1:0.5.

It has been found to be particularly advantageous to perform the reaction of step a) at elevated temperatures, i.e. above 300° C., especially above 320° C., especially in the range of 350° C. and 500° C., preferably in the range of 390° C. and 500° C.

A preferred embodiment of the invention relates to a process for preparing 2-methyl-4-phenyl-2-butanol, comprising a) the reaction of styrene with isopropanol at elevated temperature, where the molar ratio of the styrene used in step a) to the isopropanol used in step a) is in the range from 1:below 5 to 1:0.5, and where the temperature is greater than or equal to 390° C., especially greater than or equal to 450° C.

For the rest, the preferred reaction conditions specified above under step a) apply to this further subject of the invention.

It has been found that, surprisingly, with the process according to the invention, it is also possible to employ significantly greater ratios of styrene to isopropanol compared to the prior art without occurrence of any greater conversion or yield losses. This is also enabled by the fact that, with the process according to the invention, unwanted formation of polystyrene is reduced—thus, more styrene monomer is available to the reaction, and shifts in the reaction system are prevented.

The reaction mixture obtained in step a) can be worked up in a manner known per se or be used directly as such in step b) of the process according to the invention. In general, it has been found to be advantageous to work up the reaction mixture obtained in step a), for example by extraction or distillation or by a combination of these measures. In one embodiment of the process according to the invention, the reaction mixture obtained in step a) is worked up by distillation to remove the desired 2-methyl-4-phenyl-2-butanol as the medium fraction from low and high boilers. When working with an isopropanol excess, the low boiler fraction consisting predominantly of isopropanol can be recycled into the process. In general, isopropanol will be substantially removed before step b), such that the proportion of isopropanol in the reactant used for hydrogenation in step b) is less than 20% by weight, especially not more than 10% by weight, based on the total amount of reactant in step b).

According to the configuration of the distillation, pure methyl-4-phenyl-2-butanol is obtained (purity ≥95% by weight, particularly ≥98% by weight and especially ≥99% by weight or ≥99.5% by weight), or a composition which consists essentially, i.e. to an extent of at least 95% by weight, particularly at least 98% by weight and especially at least 99% by weight or at least 99.5% by weight, of 2-methyl-4-phenyl-2-butanol and small amounts of 2-methyl-4-phenyl-2-pentanol, for example compositions in which the weight ratio of 2-methyl-4-phenyl-2-butanol to 2-methyl-4-phenyl-2-pentanol is in the range from 50:1 to 1000:1. Both the pure 2-methyl-4-phenyl-2-butanol and the composition which consists essentially of 2-methyl-4-phenyl-2-butanol and small amounts of 2-methyl-4-phenyl-2-pentanol can be used in the subsequent hydrogenation in step b), and give correspondingly pure 4-cyclohexyl-2-methyl-2-butanol (purity ≥95% by weight, particularly ≥98% by weight and especially ≥99% by weight or ≥99.5% by weight), or a composition which consists essentially, i.e. to an extent of at least 95% by weight, particularly at least 98% by weight and especially at least 99% by weight or at least 99.5% by weight of 4-cyclohexyl-2-methyl-2-butanol, and small amounts of 4-cyclohexyl-2-methyl-2-pentanol, for example compositions in which the weight ratio of 4-cyclohexyl-2-methyl-2-butanol to 4-cyclohexyl-2-methyl-2-pentanol is in the range from 50:1 to 1000:1.

The 2-methyl-4-phenyl-2-butanol obtained in step a) is subsequently subjected, in step b) of the process according to the invention, to a heterogeneously catalyzed hydrogenation over a catalyst suitable for ring hydrogenation of aromatics, which is also referred to hereinafter as catalyst.

Suitable catalysts are in principle all catalysts known to be suitable for ring hydrogenation of aromatics, i.e. catalysts which catalyze the hydrogenation of phenyl groups to cyclohexyl groups. These are typically catalysts which comprise at least one active metal from group VIIIB of the Periodic Table (CAS version), for example palladium, platinum, iron, cobalt, nickel, rhodium, iridium, ruthenium, especially ruthenium, rhodium or nickel, or a mixture of two or more thereof, optionally in combination with one or more further active metals. Preferred further active metals are selected from groups IB and VIIB of the Periodic Table (CAS version). Among the likewise usable metals of transition groups IB and/or VIIB of the Periodic Table of the Elements, for example, copper and/or rhenium are suitable.

The catalysts may be unsupported catalysts or preferably supported catalysts. Suitable support materials are, for example, activated carbon, silicon carbide, silicon dioxide, aluminum oxide, magnesium oxide, titanium dioxide, zirconium dioxide, aluminosilicates and mixtures of these support materials. The amount of active metal is typically 0.05 to 10% by weight, frequently 0.1 to 7% by weight and especially 4 to 7% by weight, preferably 5 to 7% by weight, based on the total weight of the supported catalyst, especially when the active metal is a noble metal such as rhodium, ruthenium, platinum, palladium or iridium. In catalysts which comprise cobalt and/or nickel as active metals, the amount of active metal may be up to 100% by weight and is typically in the range from 1 to 100% by weight, especially 10 to 90% by weight, based on the total weight of the catalyst.

The supported catalysts can be used in the form of a powder. In general, such a powder has particle sizes in the range from 1 to 200 µm, especially 1 to 100 µm. Pulverulent catalysts are suitable especially when the catalyst is suspended in the reaction mixture to be hydrogenated (suspension mode). In the case of use of the catalysts in fixed catalyst beds, it is customary to use shaped bodies, which may have, for example, the shape of spheres, tablets, cylinders, strands, rings or hollow cylinders, stars and the like. The dimensions of these shaped bodies vary typically within the range from 0.5 mm to 25 mm. Frequently, catalyst extrudates with extrudate diameters of 1.0 to 5 mm and extrudate lengths of 2 to 25 mm are used. It is generally possible to achieve higher activities with smaller extrudates, but these typically do not have sufficient mechanical stability in the hydrogenation process. Therefore, very particular preference is given to using extrudates with extrudate diameters in the range from 1.5 to 3 mm. Likewise preferred are spherical support materials with sphere diameters in the range from 1 to 10 mm, especially 2 to 6 mm.

Preferred catalysts are those which comprise at least one active metal selected from ruthenium, rhodium and nickel, and optionally in combination with one or more further active metals selected from groups IB, VIIB or VIIIB of the Periodic Table (CAS version).

Particularly preferred catalysts are ruthenium catalysts. These comprise ruthenium as the active metal, optionally in combination with one or more further active metals.

Preferred further active metals are selected from groups IB, VIIB or VIIIB of the Periodic Table (CAS version). The catalysts are unsupported catalysts or preferably supported catalysts. Examples of further active metals from group VIIIB are, for example, platinum, rhodium, palladium, iridium, iron, cobalt or nickel, or a mixture of two or more thereof. Among the likewise usable metals of transition groups IB and/or VIIB of the Periodic Table of the Elements, for example, copper and/or rhenium are suitable. Preference is given to using ruthenium alone as the active metal, or together with platinum or iridium as the active metal; very particular preference is given to using ruthenium alone as the active metal.

Preference is given especially to ruthenium catalysts in which the ruthenium is arranged on support material, called supported ruthenium catalysts. The support materials of such supported catalysts generally have a BET surface area, determined by $N_2$ adsorption to DIN 66131, of at least 30 $m^2/g$, especially 50 to 1500 $m^2/g$, preferably 800 to 1200 $m^2/g$. Preference is given to silicon dioxide-containing support materials, especially those which have a silicon dioxide content of at least 90% by weight, based on the total weight of the support material. Likewise preferred are aluminum oxide-containing support materials, especially those which have an aluminum oxide content (calculated as $Al_2O_3$) of at least 90% by weight, based on the total weight of the support material.

Activated carbon support materials are likewise preferred, these being commercially available, for example, under the "Norit SX plus" trade name from Norit.

Suitable ruthenium catalysts are the catalysts specified, for example, in U.S. Pat. No. 3,027,398, DE 4407091, EP 258789, EP 813906, EP 1420012, WO 99/32427, WO 00/78704, WO 02/100536, WO 03/103830, WO 2005/61105, WO 2005/61106, WO 2006/136541, EP 1317959, and that specified in EP 09179201.0, which was yet to be published at the priority date of the present application. With regard to the catalysts disclosed therein, reference is made to these documents.

Equally preferred catalysts are rhodium catalysts. These comprise rhodium as an active metal, optionally in combination with one or more further active metals. Preferred further active metals are selected from groups IB, VIIB or VIIIB of the Periodic Table (CAS version). The catalysts may be unsupported catalysts or preferably supported catalysts. Examples of further active metals are from the group VIIIB are, for example, platinum, palladium, iridium, iron, cobalt or nickel, or a mixture of two or more thereof. Among the likewise useable metals of transition groups IB and/or VIIB of the Periodic Table of the Elements, copper and/or rhenium, for example, are suitable. In these catalysts, preference is given to using rhodium alone as the active metal. Suitable rhodium catalysts are known, for example, from the publications cited above for ruthenium catalysts, or can be prepared by the procedures specified therein, or are commercially available, for example the catalyst Escat 34 from Engelhard.

Equally preferred catalysts are nickel catalysts. These comprise nickel as an active metal, optionally in combination with one or more further active metals. Preferred further active metals are selected from groups IB, VIIB or VIIIB of the Periodic Table (CAS version). The catalysts may be unsupported catalysts or preferably supported catalysts. Examples of further active metals are from the group VIIIB are, for example, platinum, palladium, iridium, iron or cobalt, or a mixture of two or more thereof. Among the likewise useable metals of transition groups IB and/or VIIB of the Periodic Table of the Elements, copper and/or rhenium, for example, are suitable. In these catalysts, preference is given to using nickel alone as the active metal. Suitable nickel catalysts are commercially available, for example BASF catalyst Ni5249P.

The catalyst used in step b) is more preferably a supported catalyst which comprises, as an active metal, ruthenium alone or together with at least one further active metal of transition groups IB, VIIB or VIIIB of the Periodic Table of the Elements (CAS version) on a support material. Preference is given to using ruthenium alone as the active metal or together with iron, platinum or iridium as the active metal; very particular preference is given to using ruthenium alone or in a combination with iron as the active metal. Useful support materials for the supported ruthenium catalysts are in principle the aforementioned support materials. Preference is given to silicon dioxide-containing support materials, especially those which have a silicon dioxide content of at least 90% by weight, based on the total weight of the support material. Preference is likewise given to aluminum oxide-containing support materials, especially those which have an aluminum oxide content (calculated as $Al_2O_3$) of at least 90% by weight, based on the total weight of the support material. Preference is given to support materials having a specific BET surface area, determined by $N_2$ adsorption to DIN 66131, of at least 30 $m^2/g$, especially 50 to 1500 $m^2/g$, especially 800 to 1200 $m^2/g$. The amount of active metal is typically 0.05 to 10% by weight, preferably 0.1 to 3% by weight and especially 0.1 to 1% by weight, based on the total weight of the supported ruthenium catalyst. Activated carbon support materials are likewise preferred, these being commercially available, for example, under the "Norit SX plus" trade name from Norit.

Likewise preferably, the catalyst used in step b) is a supported catalyst which comprises, as an active metal, rhodium alone or together with at least one further active metal of transition groups IB, VIIB or VIIIB of the Periodic Table of the Elements (CAS version) on a support material. Preference is given to using rhodium alone as the active metal or together with platinum or iridium as the active metal; very particular preference is given to using rhodium alone as the active metal. Useful support materials for the supported rhodium catalysts are in principle the aforementioned support materials. Preference is given to silicon dioxide-containing support materials, especially those which have a silicon dioxide content of at least 90% by weight, based on the total weight of the support material. Preference is likewise given to aluminum oxide-containing support materials, especially those which have aluminum oxide content (calculated as $Al_2O_3$) of at least 90% by weight, based on the total weight of the support material. The amount of active metal is typically 0.05 to 10% by weight, based on the total weight of the supported rhodium catalyst.

Likewise preferably, the catalyst used in step b) is a catalyst which comprises, as an active metal, nickel alone or together with at least one further active metal of transition groups IB, VIIB or VIIIB of the Periodic Table of the Elements (CAS version), optionally on a support material. Preference is given to using nickel alone as the active metal. Useful support materials for the supported nickel catalysts are in principle the aforementioned support materials. Preference is given to silicon dioxide-, aluminum oxide- and magnesium oxide-containing support materials, especially those which consist to an extent of at least 90% by weight of such materials. The amount of active metal is typically 1 to 90% by weight, preferably 10 to 80% by weight and especially 30 to 70% by weight, based on the total weight of the supported nickel catalyst. Preference is also given to those nickel catalysts which consist essentially exclusively of active metal, i.e. wherein the amount of active metal is more than 90% by weight, e.g. 90 to 100% by weight.

In a particularly preferred embodiment, a shell catalyst is used, especially a shell catalyst which has, as the active metal, ruthenium alone or together with at least one further active metal of transition groups IB, VIIB or VIIIB of the Periodic Table of the Elements in the amounts specified above. Such shell catalysts are known especially from WO 2006/136541, and in EP 09179201.0, which was yet to be published at the priority date of the present application.

Such a shell catalyst is a supported catalyst wherein the predominant amount of the active metal(s) present in the catalyst is close to the surface of the catalyst. In particular, at least 60% by weight, more preferably at least 80% by weight, based in each case on the total amount of the active metal, is present down to a penetration depth of not more than 200 μm, i.e. in a shell with a distance of not more than 200 μm from the surface of the catalyst particles. In contrast, only a very small amount, if any, of the active metal is present in the interior (core) of the catalyst. Very particular preference is given to an inventive shell catalyst in which no active metal can be detected in the interior of the catalyst, i.e. active metal is present only in the outermost shell, for example in a zone down to a penetration depth of 100 to 200 μm. The aforementioned data can be determined by means of SEM (scanning electron microscopy), EPMA (electron probe microanalysis)–EDXS (energy dispersive X-ray spectroscopy), and are averaged values. Further data with regard to the aforementioned test methods and techniques can be found, for example, in "Spectroscopy in Catalysis" by J. W. Niemantsverdriet, VCH, 1995. For further details regarding the penetration depth of active metal, reference is made to WO 2006/136541, especially to page 7 lines 6 to 12.

Preferred shell catalysts have a content of active metal in the range from 0.05 to 1% by weight, especially 0.1 to 0.5% by weight, more preferably 0.25 to 0.35% by weight, based in each case on the total weight of the catalyst.

For the inventive hydrogenation in step b), particular preference is given to shell catalysts with a support material based on silicon dioxide, generally amorphous silicon dioxide. The term "amorphous" in this context is understood to mean that the proportion of crystalline silicon dioxide phases makes up less than 10% by weight of the support material. The support materials used to prepare the catalysts may, however, have superstructures which are formed via regular arrangement of pores in the support material. Useful support materials are in principle amorphous silicon dioxide types which consist at least to an extent of 90% by weight of silicon dioxide, where the remaining 10% by weight, preferably not more than 5% by weight, of the support material may also be another oxidic material, for example MgO, CaO, $TiO_2$, $ZrO_2$, $Fe_2O_3$ and/or alkali metal oxide. In a preferred embodiment of the shell catalyst, the support material is halogen-free, especially chlorine-free, i.e. the content of halogen in the support material is less than 500 ppm by weight, for example in the range from 0 to 400 ppm by weight. Thus, a preferred shell catalyst is one which comprises less than 0.05% by weight of halide (determined by ion chromatography), based on the total weight of the catalyst. Preference is given to support materials which have a specific surface area in the range from 30 to 700 $m^2/g$, preferably 30 to 450 $m^2/g$ (BET surface area to DIN 66131). Suitable amorphous support materials based on silicon dioxide are familiar to those skilled in the art and are commercially available (see, for example, O. W. Flörke, "Silica" in Ullmann's Encyclopedia of Industrial Chemistry, 6th Edition on CD-ROM). They may either be of natural origin or may have been produced synthetically. Examples of suitable amorphous support materials based on silicon dioxide are silica gels, kieselguhr, fumed silicas and precipitated silicas. In a preferred embodiment of the invention, the catalysts have silica gels as support materials. According to the configuration of the shell catalyst, the support material may have different shapes. When the process in which the inventive shell catalysts are used is configured as a suspension process, the inventive catalysts will typically be prepared using the support material in the form of a fine powder. The powder preferably has particle sizes in the range from 1 to 200 µm, especially 1 to 100 µm. In the case of use of the inventive shell catalyst in fixed catalyst beds, it is customary to use shaped bodies of the support material, which are obtainable, for example, by extrusion or tableting, and which may have, for example, the form of spheres, tablets, cylinders, extrudates, rings or hollow cylinders, stars and the like. The dimensions of these shaped bodies typically vary within the range from 0.5 mm to 25 mm. Frequently, catalyst extrudates with extrudate diameters of 1.0 to 5 mm and extrudate lengths of 2 to 25 mm are used. It is generally possible to achieve higher activities with smaller extrudates; these, however, often do not have sufficient mechanical stability in the hydrogenation process. Therefore, very particular preference is given to using extrudates with extrudate diameters in the range from 1.5 to 3 mm. Preference is likewise given to spherical support materials with sphere diameters in the range from 1 to 10 mm, especially 2 to 6 mm.

In a particularly preferred embodiment of the shell catalysts, the support material of the catalyst, which is especially a support material based on silicon dioxide, has a pore volume in the range from 0.6 to 1.0 ml/g, preferably in the range from 0.65 to 0.9 ml/g, for example 0.7 to 0.8 ml/g, determined by Hg porosimetry (DIN 66133), and a BET surface area in the range from 280 to 500 $m^2/g$, preferably in the range from 280 to 400 $m^2/g$, most preferably in the range from 300 to 350 $m^2/g$. In such shell catalysts, at least 90% of the pores present preferably have a diameter of 6 to 12 nm, preferably 7 to 11 nm, more preferably 8 to 10 nm. The pore diameter can be determined by processes known to those skilled in the art, for example by Hg porosimetry or $N_2$ physisorption. In a preferred embodiment, at least 95%, more preferably at least 98%, of the pores present have a pore diameter of 6 to 12 nm, preferably 7 to 11 nm, more preferably 8 to 10 nm. In a preferred embodiment, no pores smaller than 5 nm are present in these shell catalysts. Furthermore, there are preferably no pores larger than 25 nm, especially larger than 15 nm, in these shell catalysts. In this composition, "no pores" means that no pores with these diameters can be found by customary test methods, for example Hg porosimetry or $N_2$ physisorption.

In preferred shell catalysts, the dispersity of the active metal is preferably 30 to 60%, more preferably 30 to 50%. Processes for measuring the dispersity of the active metal are known per se to those skilled in the art, for example by pulse chemisorption, the determination of the noble metal dispersion (specific metal surface area, crystal size) being carried out by the CO pulse method (DIN 66136(1-3)).

The hydrogenation process according to the invention can be performed in the liquid phase or in the gas phase. Preference is given to performing the hydrogenation process according to the invention in the liquid phase.

The hydrogenation process according to the invention can be performed in the absence of a solvent or diluent or in the presence of a solvent or diluent, i.e. it is not necessary to perform the hydrogenation in solution. The solvent or diluent used may be any suitable solvent or diluent. Useful solvents or diluents are in principle those which are capable of very substantially dissolving the organic compounds to be hydrogenated, or mix completely therewith, and which are inert under the hydrogenation conditions, i.e. are not hydrogenated. Examples of suitable solvents are cyclic and acyclic ethers having preferably 4 to 8 carbon atoms, for example tetrahydrofuran, dioxane, methyl tert-butyl ether, dimethoxyethane, dimethoxypropane, dimethyldiethylene glycol, aliphatic alcohols having preferably 1 to 6 carbon atoms, such as methanol, ethanol, n- or isopropanol, n-, 2-, iso- or tert-butanol, carboxylic esters of aliphatic carboxylic acids having preferably 3 to 8 carbon atoms, such as methyl acetate, ethyl acetate, propyl acetate or butyl acetate, methyl propionate, ethyl propionate, butyl propionate, and aliphatic ether alcohols such as methoxypropanol, and cycloaliphatic compounds such as cyclohexane, methylcyclohexane and dimethylcyclohexane. The amount of the solvent or diluent used is not particularly restricted and can be selected freely as required, although, when using a solvent, preference is given to those amounts which lead to a 3 to 70% by weight solution of the organic compound intended for hydrogenation.

In one embodiment of the invention, step b) of the invention is performed in substance.

The actual hydrogenation is effected typically in analogy to the known hydrogenation processes for hydrogenating organic compounds which have hydrogenatable groups, preferably for hydrogenating a carbocyclic aromatic group to the corresponding carbocyclic aliphatic group, as described in the prior art cited at the outset. For this purpose, the organic compound as a liquid phase or gas phase, preferably as a liquid phase, is contacted with the catalyst in the presence of hydrogen. The liquid phase can be passed over a moving catalyst bed (moving bed mode) or a fixed catalyst bed (fixed bed mode).

The hydrogenation can be configured either continuously or batchwise, preference being given to the continuous process regime. The process according to the invention is preferably performed in trickle reactors or in flooded mode by the fixed bed mode, particular preference being given to performance in trickle reactors. More particularly, the compound to be hydrogenated here is used in substance, i.e. substantial absence of organic diluents (solvent content preferably <10%). The hydrogenation can be passed over the catalyst either in cocurrent with the solution of the reactant to be hydrogenated or in countercurrent. The hydrogenation can also be performed batchwise in batchwise mode. In this case, the hydrogenation will preferably be performed in an organic solvent or diluent.

In a further embodiment of the invention the hydrogenation can be conducted in suspension mode, especially in continuous suspension mode.

In the case of batchwise performance of the process according to the invention, in step B, the catalyst is typically used in an amount such that the concentration of ruthenium in the reaction mixture used for hydrogenation is in the range from 10 to 10 000 ppm, especially in the range from 50 to 5000 ppm, especially in the range from 100 to 1000 ppm.

The hydrogenation is effected typically at a hydrogen pressure in the range from 5 to 50 MPa, especially in the range from 10 to 30 MPa. The hydrogen can be fed into the reactor as such, or diluted with an inert, for example nitrogen or argon.

The hydrogenation in step b) is effected typically at temperatures above 50° C., especially in the range from 100 to 250° C.

Apparatus suitable for performing the hydrogenation is known to those skilled in the art and is guided primarily by the mode of operation. Suitable apparatus for performing a hydrogenation according to the hydrogenation over a moving catalyst bed and over a fixed catalyst bed are known, for example, from Ullmanns Enzyklopädie der Technischen Chemie, 4th edition, volume 13, p. 135 ff., and from P. N. Rylander, "Hydrogenation and Dehydrogenation" in Ullmann's Encyclopedia of Industrial Chemistry, 5th ed. on CD-ROM.

It has been found that, surprisingly, step a) of the process according to the invention affords not only 2-methyl-4-phenyl-2-butanol but also 2-methyl-4-phenyl-2-pentanol when it is performed under conditions under which isopropanol is present under supercritical conditions, especially when the molar ratio of styrene to isopropanol is in the range from 1:below 5 to 1:0.5, particularly in the range from 1:4.9 to 1:0.5 especially 1:4.5 to 1:0.5, more preferably in the range from 1:4 to 1:0.75 and especially in the range from 1:3.5 to 1:1.5, especially 1:2 to 1:1.

In a preferred embodiment, the process according to the invention is performed in semibatchwise mode.

Such a process is novel and likewise forms part of the subject matter of the present invention. Accordingly, the invention relates to a process for preparing a composition comprising 2-methyl-4-phenyl-2-butanol and 2-methyl-4-phenyl-2-pentanol, comprising the reaction of styrene with isopropanol at elevated temperature under conditions under which isopropanol is present under supercritical conditions, the molar ratio of styrene to isopropanol being in the range from 1:below 10, preferably 1:9 to 1:0.5, preferably 1:5 to 1:0.5, particularly in the range from 1:4.5 to 1:0.5, more preferably in the range from 1:4 to 1:0.75 and especially in the range from 1:3.5 to 1:1.5, especially 1:2 to 1:1.

It has been found to be advantageous when the reaction is performed in semibatchwise mode or continuously, as already described above for step a). For this purpose, it has been found to be especially advantageous when at least 80%, especially at least 90%, of the isopropanol used is initially charged, optionally together with a portion of the styrene, and at least 80%, especially at least 90%, of the styrene used is supplied to the reaction under reaction conditions. The styrene can be added in portions or preferably continuously. The rate with which the styrene is supplied is preferably selected such that the molar ratio of the styrene fed into the reaction zone or the reactor to the isopropanol present in the reaction zone is in the range from 1:below 10, preferably 1:9 to 1:0.5, preferably 1:5 to 1:0.5, particularly in the range from 1:4.5 to 1:0.5, more preferably in the range from 1:4 to 1:0.75 and especially in the range from 1:3.5 to 1:1.5, especially 1:2 to 1:1. This is especially true, in a continuous reaction regime too, of the molar ratios of styrene and isopropanol supplied to the reactor or to the reaction zone.

Otherwise, the conditions specified above for step a) also apply in the same way to the process according to the invention for preparing a composition comprising 2-methyl-4-phenyl-2-butanol and 2-methyl-4-phenyl-2-pentanol. Reference is therefore made to these details in full.

Such a process affords compositions which comprise 2-methyl-4-phenyl-2-butanol and 2-methyl-4-phenyl-2-pentanol. The weight ratio of 2-methyl-4-phenyl-2-butanol to 2-methyl-4-phenyl-2-pentanol in such compositions is typically in the range from 50:1 to 1000:1.

The reaction mixture obtained in the preparation of a composition comprising 2-methyl-4-phenyl-2-butanol and 2-methyl-4-phenyl-2-pentanol by reaction of styrene with isopropanol can be worked up in the manner described above for step a). Reference is made completely to the details given above for workup of the reaction mixture obtained in step a). More particularly, the reaction mixture obtained is worked up by distillation, in which case the desired composition consisting essentially of 2-methyl-4-phenyl-2-butanol and 2-methyl-4-phenyl-2-pentanol is removed as the middle fraction from low and high boilers. In general, a composition is then obtained which consists essentially, i.e. to an extent of at least 95% by weight, particularly at least 98% by weight and especially at least 99% by weight or at least 99.5% by weight of 2-methyl-4-phenyl-2-butanol, and small amounts of 2-methyl-4-phenyl-2-pentanol, for example compositions in which the weight ratio of 2-methyl-4-phenyl-2-butanol to 2-methyl-4-phenyl-2-pentanol in the range from 50:1 to 1000:1.

Such mixtures of 2-methyl-4-phenyl-2-butanol and small amounts of 2-methyl-4-phenyl-2-pentanol can subsequently be hydrogenated in analogy to step b) to obtain compositions comprising 4-cyclohexyl-2-methyl-2-butanol and small amounts of 4-cyclohexyl-2-methyl-2-pentanol, for example compositions in which the weight ratio of 4-cyclohexyl-2-methyl-2-butanol to 4-cyclohexyl-2-methyl-2-pentanol is in the range from 50:1 to 1000:1. Reference is made completely to the details given above for the hydrogenation in step b). Since, in one embodiment of the invention, an isopropanol excess can be employed in the preparation of a composition comprising 2-methyl-4-phenyl-2-butanol and 2-methyl-4-phenyl-2-pentanol, the low boiler fraction, which consists predominantly of isopropanol, can be recycled into the process in this embodiment. In general, isopropanol will be substantially removed before the hydrogenation, such that the proportion of isopropanol in the reactant used for the hydrogenation is less than 20% by weight, especially not more than 10% by weight, based on the total amount of reactant.

Compositions comprising 2-methyl-4-phenyl-2-butanol and 2-methyl-4-phenyl-2-pentanol are surprisingly notable in that they have a more flowery odor note compared to 2-methyl-4-phenyl-2-butanol. In these compositions, the weight ratio of 2-methyl-4-phenyl-2-butanol to 2-methyl-4-phenyl-2-pentanol is in the range from 50:1 to 1000:1. A specific composition is that of concentrates, i.e. compositions which consist essentially, i.e. to an extent of at least 95% by weight, particularly at least 98% by weight and especially at least 99% by weight or at least 99.5% by weight of 2-methyl-4-phenyl-2-butanol and small amounts of 2-methyl-4-phenyl-2-pentanol, for example compositions in which the weight ratio of 2-methyl-4-phenyl-2-butanol to 2-methyl-4-phenyl-2-pentanol is in the range from 50:1 to 1000:1. Compositions in which the weight ratio of 2-methyl-4-phenyl-2-butanol to 2-methyl-4-phenyl-2-pentanol is outside the range specified here can be prepared by mixing 2-methyl-4-phenyl-2-butanol (Muguet alcohol) with the desired amount of 2-methyl-4-phenyl-2-pentanol.

Such compositions, especially the aforementioned concentrates, can be used as fragrances or aromas for the reasons mentioned above, especially in cosmetic compositions and in washing or cleaning compositions.

It has additionally been found in the context of this invention that 2-methyl-4-phenyl-2-pentanol can also be prepared in a controlled manner by reacting α-methylstyrene with isopropanol under the conditions specified above for step a).

The invention therefore also provides a process for preparing 2-methyl-4-phenyl-2-pentanol, in which α-methylstyrene is reacted with isopropanol at elevated temperature, where the molar ratio of the α-methylstyrene used to the isopropanol used is in the range from 1:below 5 to 1:0.5, preferably in the range from 1:4.9 to 1:0.5, particularly in the range from 1:4.5 to 1:0.5, more preferably in the range from 1:4 to 1:0.75 and especially in the range from 1:3.5 to 1:1.5, especially 1:2 to 1:1.

For the reaction of α-methylstyrene with isopropanol, essentially all details apply which have been given above and in the claims for the reaction of styrene with isopropanol in step a). Reference is therefore made completely to these details.

Alternatively, 2-methyl-4-phenyl-2-pentanol or a mixture consisting essentially of 2-methyl-4-phenyl-2-pentanol can be obtained by distillative separation of mixtures comprising 2-methyl-4-phenyl-2-butanol and 2-methyl-4-phenyl-2-pentanol, for example by distillative separation of mixtures as obtained in step a) of the process according to the invention.

2-Methyl-4-phenyl-2-pentanol is likewise an odorant and can therefore be used in all applications for odorants of this type. As already stated above, it can surprisingly also be used for modification of the odor properties of 2-methyl-4-phenyl-2-butanol.

2-Methyl-4-phenyl-2-pentanol can be subjected to a hydrogenation in analogy to step b). This gives 4-cyclohexyl-2-methyl-2-pentanol in a high yield.

4-Cyclohexyl-2-methylpentanol is, similarly to 4-cyclohexyl-2-methyl-2-butanol, an odorant. In addition, it can surprisingly be used for modification of the odor properties of other odorants, especially of 4-cyclohexyl-2-methyl-2-butanol. 4-Cyclohexyl-2-methyl-2-pentanol can therefore be used as a fragrance or aroma, especially in cosmetic compositions and in washing or cleaning compositions.

In these compositions, the weight ratio of 4-cyclohexyl-2-methyl-2-butanol to 4-cyclohexyl-2-methyl-2-pentanol is generally in the range from 50:1 to 1000:1. Such compositions may also comprise small amounts of 4-cyclohexyl-2-methylbutane and possibly 4-cyclohexyl-2-methylpentane, which are obtained by over-reduction of 2-methyl-4-phenyl-2-butanol and 2-methyl-4-phenyl-2-pentanol respectively. The proportion by weight of the total amount of cyclohexyl-2-methylbutane and any 4-cyclohexyl-2-methylpentane will generally not exceed 10% by weight, especially 5% by weight, based on 4-cyclohexyl-2-methyl-2-butanol, and is, if present, in the range from 0.01 to 10% by weight, especially in the range from 0.01 to 5% by weight, based on 4-cyclohexyl-2-methyl-2-butanol. It is of course also possible to remove cyclohexyl-2-methylbutane and any 4-cyclohexyl-2-methylpentane, for example by a distillative route, such that the total amount of cyclohexyl-2-methylbutane and any 4-cyclohexyl-2-methylpentane is less than 1% by weight, especially less than 0.5% by weight or less than 0.1% by weight, based on 4-cyclohexyl-2-methyl-2-butanol. A specific composition is that of concentrates, i.e. compositions which consist essentially, i.e. to an extent of at least 95% by weight, particularly at least 98% by weight and especially at least 99% by weight or at least 99.5% by weight of 4-cyclohexyl-2-methyl-2-butanol and small amounts of 4-cyclohexyl-2-methyl-2-pentanol, for example compositions in which the weight ratio of 4-cyclohexyl-2-methyl-2-butanol to 4-cyclohexyl-2-methyl-2-pentanol is in the range from 50:1 to 1000:1.

These concentrates may comprise cyclohexyl-2-methylbutane and possibly 4-cyclohexyl-2-methylpentane in the amounts mentioned above. Compositions in which the weight ratio of 4-cyclohexyl-2-methyl-2-butanol to 4-cyclohexyl-2-methyl-2-pentanol is outside the range specified here can be prepared by mixing cyclohexyl-2-methyl-2-butanol with the desired amount of 4-cyclohexyl-2-methyl-2-pentanol.

Such compositions, especially the aforementioned concentrates, can be used as fragrances or aromas for the reasons mentioned above, especially in cosmetic compositions and in washing or cleaning compositions.

As already stated above, 4-cyclohexyl-2-methyl-2-pentanol can be prepared from 2-methyl-4-phenyl-2-pentanol in analogy to step b), i.e. by a process comprising a heterogeneously catalyzed hydrogenation of 2-methyl-4-phenyl-2-pentanol over a catalyst suitable for ring hydrogenation of aromatics. Such a process likewise forms part of the subject matter of the present invention. With regard to the hydrogenation of 2-methyl-4-phenyl-2-pentanol, reference is made completely to the details given above for the hydrogenation in step b).

The procedure here may be first to prepare 2-methyl-4-phenyl-2-pentanol in a controlled manner and then to subject it to a heterogeneously catalyzed hydrogenation over a catalyst suitable for ring hydrogenation of aromatics, in analogy to step b) described above.

However, the procedure may also be first to prepare a composition composed of 2-methyl-4-phenyl-2-butanol and 2-methyl-4-phenyl-2-pentanol, for example in the manner described above for step a), to subject this composition to a heterogeneously catalyzed hydrogenation over a catalyst suitable for ring hydrogenation of aromatics in analogy to the above-described step b), and to separate the composition obtained, which comprises 4-cyclohexyl-2-methyl-2-butanol and 4-cyclohexyl-2-methyl-2-pentanol, into its constituents by distillation.

Accordingly, the invention also relates to a process for preparing 4-cyclohexyl-2-methyl-2-pentanol, comprising the following steps:
a') preparation of a composition comprising 2-methyl-4-phenyl-2-butanol and 2-methyl-4-phenyl-2-pentanol by reaction of styrene with isopropanol at elevated temperature under conditions under which isopropanol is present under supercritical conditions, the molar ratio of styrene to isopropanol being in the range from 1:below 10 to 1:0.5, preferably in the range from 1:9 to 1:0.5, particularly in the range from 1:5 to 1:0.5, especially in the range from 1:4.5 to 1:0.5, more preferably in the range from 1:4 to 1:0.75 and especially in the range from 1:3.5 to 1:1.5, especially 1:2 to 1:1;
b') heterogeneously catalyzed hydrogenation of the composition obtained in step a) over a catalyst suitable for ring hydrogenation of aromatics; and
c) distillative workup of the composition obtained in step b') to obtain a composition consisting essentially, i.e. to an extent of at least 90% by weight, especially to an extent of at least 95% by weight, of 4-cyclohexyl-2-methyl-2-pentanol.

Accordingly, the invention further relates to a process for preparing 4-cyclohexyl-2-methyl-2-pentanol, comprising the following steps:
a') preparation of a composition comprising 2-methyl-4-phenyl-2-butanol and 2-methyl-4-phenyl-2-pentanol by reaction of styrene with isopropanol at elevated temperature under conditions under which isopropanol is present under supercritical conditions, the molar ratio of styrene to isopropanol being in the range from 1:below 10 to 1:0.5, preferably in the range from 1:9 to 1:0.5, particularly in the range from 1:5 to 1:0.5, especially in the range from 1:4.5 to 1:0.5, more preferably in the range from 1:4 to 1:0.75 and especially in the range from 1:3.5 to 1:1.5, especially 1:2 to 1:1.
c') distillative workup of the composition obtained in step a') to obtain a composition consisting predominantly of 2-methyl-4-phenyl-2-pentanol
b') heterogeneously catalyzed hydrogenation of the composition obtained in step c') over a catalyst suitable for ring hydrogenation of aromatics; and optionally
c") distillative workup of the composition obtained in step b') to obtain a composition consisting essentially of 4-cyclohexyl-2-methyl-2-pentanol.

It will be appreciated that step a') is performed in analogy to the step a) already described above. To that extent, for step a'), reference is made completely to the details given for step a).

It will also be appreciated that step b') is performed in analogy to the step ab) already described above. To that extent, for step b'), reference is made completely to the remarks made for step b).

The distillative steps c), c') and c") can be performed in analogy to customary processes for fractional distillation. Suitable apparatus for this purpose is familiar to those skilled in the art. The necessary conditions can be determined by routine experiments. In general, distillation is effected under reduced pressure.

In addition, the invention additionally relates to a process for preparing 4-cyclohexyl-2-methyl-2-pentanol, comprising the following steps:
a") reaction of α-methylstyrene with isopropanol at elevated temperature to obtain 2-methyl-4-phenyl-2-pentanol, and
b") heterogeneously catalyzed hydrogenation of 2-methyl-4-phenyl-2-pentanol over a catalyst suitable for ring hydrogenation of aromatics, where the molar ratio of the α-methylstyrene used in step a") to the isopropanol used in step a") is in the range from 1:below 5 to 1:0.5, preferably in the range from 1:4.9 to 1:0.5, particularly in the range from 1:4.5 to 1:0.5, more preferably in the range from 1:4 to 1:0.75 and especially in the range from 1:3.5 to 1:1.5, especially 1:2 to 1:1.

As already explained above, step a") is performed in analogy to the step a) already described above. To that extent, for step a"), reference is made completely to the details given for step a).

It will also be appreciated that step b") is performed in analogy to the step ab) already described above. To that extent, for step b"), reference is made completely to the details given for step b).

It will also be appreciated that the reaction product obtainable in step a"), before use thereof in step b"), can be subjected to a workup in analogy to that for the reaction product obtained in step a) above, especially to a distillative workup in which low boilers and high boilers are removed, and 2-methyl-4-phenyl-2-pentanol is obtained as a medium boiler. In this regard, reference is likewise made to the details given above.

PREPARATION EXAMPLE 1

Preparation of the Hydrogenation Catalyst

The support material used was a spherical $SiO_2$ support (AF125 type from BASF SE) with a sphere diameter of 3 to 5 mm and a tapped density of 0.49 kg/l. The BET surface area was 337 $m^2$/g, and the water absorption (WA) 0.83 ml/g. For impregnation, 14.25% by weight ruthenium(III) acetate solution in acetic acid from Umicore was used.

200 g of support were initially charged in a round-bottom flask. 15 g of ruthenium acetate solution were diluted with distilled water to 150 ml (90% WA). The support material was initially charged in the distillation flask of a rotary evaporator, and the first quarter of the solution was pumped onto the support material at 3 to 6 rpm with a slightly reduced pressure. On completion of the addition, the support was left in the rotary evaporator at 3 to 6 rpm for a further 10 minutes, in order to homogenize the catalyst. This impregnation-homogenization step was repeated three times more until all of the solution had been applied to the support. The support material thus treated was dried while being agitated in the rotary tube oven at 140° C., then reduced in a hydrogen stream (20 l/h of $H_2$; 10 l/h of $N_2$) at 200° C. for 3 h, and passivated at 25° C. (5% air in $N_2$, 2 h). The inventive catalyst A thus obtained comprised 0.34% by weight of ruthenium, based on the catalyst weight.

EXAMPLE 1

Step a

The reaction was performed in a continuous laboratory plant which, as a reactor, comprised a 300 ml autoclave which was operated with pressure regulation. Thus, the amount withdrawn at any time corresponded to the amount introduced. The reaction mixture withdrawn was cooled, decompressed and collected in a discharge vessel.

A solution of styrene in isopropanol (30% by weight, 200 g/h) was pumped through the laboratory plant at a mean temperature of 410° C. in the reactor. The conversion of styrene was 85.1%, and 12.5 g/h of 2-methyl-4-phenyl-2- butanol were obtained in the steady state. The samples were analyzed by means of gas chromatography.

Step b

A 300 ml autoclave was initially charged with 10.2 g of 2-methyl-4-phenyl-2-butanol (62 mmol) from step a), dissolved in 150 ml of tetrahydrofuran, and 1.7 g of the catalyst from preparation example 1 in a catalyst basket. The autoclave was purged three times with nitrogen, and then hydrogen was injected to pressure 200 bar at 200° C. for 12 hours. After 6 and 12 hours, the progress of the reaction was analyzed by means of gas chromatography (30 m, column material DB1, internal diameter: 0.25 mm, film thickness: 0.25 μm, temperature program 50° C.-5 min isothermal; 6° C./min.→290° C.-219 min. isothermal). The product contents are reported in the table which follows.

|  | 4-Cyclohexyl-2-methyl-2-butanol | 2-Methyl-4-phenyl-2-butanol | 4-Cyclohexyl-2-methylbutane |
|---|---|---|---|
| 6 hours | 88.9% | 0% | 5.9% |
| 12 hours | 88.2% | 0% | 6.8% |

After only 6 h, no starting material was detectable any longer. The low proportion of by-products such as 4-cyclohexyl-2-methylbutane demonstrates the high selectivity of the hydrogenation for the desired target compound 4-cyclohexyl-2-methyl-2-butanol.

Step b

A 300 ml autoclave was initially charged with 100 g of a discharge from step a), which was concentrated to a 2-methyl-4-phenyl-2-butanol content of 50%, and 5 g of the catalyst according to EP1317959 example 1B. The autoclave was purged three times with nitrogen and then hydrogenation was effected at 40° C. and hydrogen pressure 150 bar for 12 hours. After 12 hours, the discharge was analyzed by means of gas chromatography (30 m column material DB1, internal diameter: 0.25 mm, film thickness: 0.25 μm, temperature program 50° C.-5 min isothermal; 6° C./min. □290° C.-219 min. isothermal). The conversion of methyl-4-phenyl-2-butanol was >99.9%; the selectivity for 4-cyclohexyl-2-methyl-2-butanol was 97.7%.

The invention claimed is:

1. A process for preparing 2-methyl-4-phenyl-2-butanol, comprising a) the reaction of styrene with isopropanol at elevated temperature, where the molar ratio of the styrene used in step a) to the isopropanol used in step a) is in the range from 1:below 5 to 1:0.5.

2. The process as claimed in claim 1, wherein the molar ratio of the styrene used in step a) to the isopropanol used in step a) is in the range from 1:4.9 to 1:0.5.

3. The process as claimed in claim 1, wherein the molar ratio of the styrene used in step a) to the isopropanol used in step a) is in the range from 1:4.5 to 1:0.5.

4. The process as claimed in claim 1, wherein the molar ratio of the styrene used in step a) to the isopropanol used in step a) is in the range from 1:4 to 1:0.75.

5. The process as claimed in claim 1, wherein the molar ratio of the styrene used in step a) to the isopropanol used in step a) is in the range from 1:3.5 to 1:1.15.

6. The process as claimed in claim 1, wherein the molar ratio of the styrene used in step a) to the isopropanol used in step a) is in the range from 1:2 to 1:1.

7. The process as claimed in claim 1, wherein the molar ratio of the styrene used in step a) to the isopropanol used in step a) is in the of 1:1.

* * * * *